US008693636B2

(12) United States Patent
Feuerlein et al.

(10) Patent No.: US 8,693,636 B2
(45) Date of Patent: Apr. 8, 2014

(54) METHOD AND X-RAY DEVICE TO DETERMINE THE VALUE OF THE TUBE VOLTAGE

(75) Inventors: Ute Feuerlein, Erlangen (DE); Sebastian Gehrsitz, Himmelstadt (DE); Christiane Koch, Eggolsheim (DE); Gerd Mayer, Gremsdorf (DE); Stefan Muehleck, Forchheim (DE); Rainer Raupach, Heroldsbach (DE)

(73) Assignee: Siemens Aktiengesellschaft, Munich (DE)

( * ) Notice: Subject to any disclaimer, the term of this patent is extended or adjusted under 35 U.S.C. 154(b) by 312 days.

(21) Appl. No.: 13/293,379

(22) Filed: Nov. 10, 2011

(65) Prior Publication Data

US 2012/0140894 A1 Jun. 7, 2012

(30) Foreign Application Priority Data

Nov. 10, 2010 (DE) .......................... 10 2010 043 712

(51) Int. Cl.
*H05G 1/32* (2006.01)

(52) U.S. Cl.
USPC ............................................ 378/112; 378/62

(58) Field of Classification Search
USPC .................. 378/62, 111, 112, 96, 97, 145
See application file for complete search history.

(56) References Cited

U.S. PATENT DOCUMENTS 7,852,986 B2 *  12/2010  Loef et al. ...................... 378/111
7,949,095 B2 *  5/2011   Ning et al. ........................ 378/62

OTHER PUBLICATIONS

"Radiation Does and Image Quality in Pediatric CT: Effect of Technical Factors and Phantom Size and Shape," Siegel et al., Radiology, vol. 233, No. 2 (2004) pp. 515-522.
"Automatic Selection of Tube Potential for Radiation Dose Reduction in CT: A General Strategy," Yu et al., Med. Phys., vol. 37, No. 1 (2010) pp. 234-243.

* cited by examiner

*Primary Examiner* — Hoon Song
(74) *Attorney, Agent, or Firm* — Schiff Hardin LLP

(57) ABSTRACT

In a method and x-ray device to determine the value of an x-ray tube voltage to generate at least one image of defined tissue to be examined, at least one provided parameter is used that establishes or describes the desired image quality; based on the dependency of the contrast of the defined tissue to be examined on the spectrum of the x-ray radiation or on the value of the tube voltage of the x-ray tube. The tube voltage is determined also based on a contrast-to-noise ratio that is constantly maintained under consideration of the aforementioned parameter such that the dose of x-ray radiation applied to the patient is optimally low upon setting the value of the tube voltage at the x-ray tube and the acquisition of at least one x-ray projection of the defined tissue.

17 Claims, 2 Drawing Sheets

METHOD AND X-RAY DEVICE TO DETERMINE THE VALUE OF THE TUBE VOLTAGE

BACKGROUND OF THE INVENTION

1. Field of the Invention

The invention concerns a method to determine the value of the tube voltage of an x-ray tube of an x-ray device in order to acquire x-ray projections in a multiphase examination of defined tissue a patient. The invention also concerns an x-ray device (in particular a computed tomography (CT) apparatus) which is designed to execute such a method. The invention also concerns a non-transitory, computer-readable data storage medium and coded with programming instructions that, when the data storage medium is loaded into a computerized control unit of an x-ray device, caused the x-ray device to be operated in accordance with a method of the above-described type.

2. Description of the Prior Art

In medical technology, when imaging with x-ray radiation, for example in computed tomography, it is always sought to apply an optimally low dose of x-ray radiation to a patient to generate one or more images of a tissue of the patient. However, a defined image quality must also be achieved in order to be able to answer the clinical question that is the reason for generating the image or images, and this requires a minimum dose. Relevant measures of image quality are the image noise or the image contrast, for example. The image contrast of defined elements and materials (such as the iodine used as a contrast agent in computed tomography) has a relatively strong dependency on the spectrum of the x-ray radiation that is used. Given the use of relatively low tube voltages, the spectrum of the x-ray radiation is such that the image contrast of iodine increases. Therefore, given the use of iodine, the dose of x-ray radiation that is applied to a patient to achieve an optimally high image quality also depends on the spectrum of the x-ray radiation.

In CT angiograms to show blood-carrying vessels, in which the visibility of iodine is of primary importance, the dose of x-ray radiation applied to a patient is therefore reduced by the use of relatively low tube voltages (see M. J. Siegel et al., "Radiation Dose and Image Quality in Pediatric CT: Effect of Technical Factors and Phantom Size and Shape", Radiology 2004; 233: Page 515 to 522).

In "Automatic selection of tube potential for radiation dose reduction in CT: A general strategy", L. Yu et al. propose a method to select a tube voltage suitable for a specific examination with regard to a reduction of the dose of x-ray radiation that is to be applied to a patient. In this method, an iodine contrast-to-noise ratio is used as an image quality index in connection with a noise constraint parameter $\alpha$ in order to be able to characterize and account for the different requirements for the image quality for different examinations. Different noise constraint parameters $\alpha$ are available for adaptation for different examinations. Using the noise constraint parameter, it is sought to make the absolute image noise not exceed a certain value. For a CT angiogram in which the iodine contrast-to-noise ratio is of primary relevance, the noise constraint parameter $\alpha$ is selected between 1.5 and 2.0. The noise constraint parameter $\alpha$ is selected between 1.1 and 1.25 for breast, torso or pelvic examinations with contrast agent, and $\alpha$ is selected equal to one for breast, torso or pelvic examinations without contrast agent. The tube voltage with which the lowest dose of x-ray radiation is applied to the patient for a specific examination is determined based on a "relative dose factor" (RDF) into which the contrast-to-noise ratio of iodine and the noise constraint parameter $\alpha$ enter.

SUMMARY OF THE INVENTION

An object of the invention is to provide a method, an x-ray device, and a computer-readable storage medium of the aforementioned type wherein the value of the tube voltage of an x-ray tube for generation of at least one image of defined tissue to be examined is determined in a manner different from the prior art, so that the dose of x-ray radiation that is applied to the patient is as small as possible.

The invention is based on the insight that, for virtually every examination of tissue with x-ray radiation with consistent image quality, a tube voltage can be found at which the dose of x-ray radiation applied to the patient in the examination of the tissue can be reduced or optimized. The optimization depends on the tissue to be examined that should be shown in at least one image.

The starting point of the method according to the invention is consideration of the dependency of the contrast of the defined tissue to be examined on the spectrum of the x-ray radiation of the x-ray tube, and thus on the value of the tube voltage that is relevant for the generated spectrum of x-ray radiation. Furthermore, an image quality required or desired for an intended diagnosis using the at least one generated image of the defined tissue to be examined, and thus for a solution of a diagnostic or clinical question, is predetermined by at least one parameter establishing or describing the desired image quality. By consideration of this at least one parameter establishing or describing the desired image quality, and with a contrast-to-noise ratio as an additional image quality feature, the tube voltage is determined that results in a dose of x-ray radiation applied to the patient that is lowest in the acquisition of one or more x-ray projections for generation of at least one image of the defined tissue to be examined of the patient.

According to a variant of intention, a reference protocol is provided for the acquisition of the at least one x-ray projection of the defined tissue to be examined. The reference protocol can have been provided by the user of the x-ray device and includes a reference tube voltage and a reference tube current as acquisition parameters for the acquisition of the at least one x-ray projection. Through the reference tube voltage and the reference tube current, reference values are provided for the desired image quality that establish a defined noise level for the tissue to be examined.

Alternatively, according to another variant of the invention, the at least one parameter to be provided that establishes or describes the desired image quality can itself be a reference noise of the image (which image is to be generated from the at least one acquired x-ray projection) of the defined tissue to be examined of the patient. In this case a reference noise level for the image noise is directly provided. The specification of both the reference tube voltage and the reference tube current, and the specification of the reference noise level, can be assisted by the x-ray device by a suggestion or prompt for selection by the user being presented based on experimental values after specification of the defined tissue to be examined. In this way the desired image quality is established for one or more images to be generated of the defined tissue to be examined.

In an embodiment of the invention, the dependency of the contrast of the examination type and/or of the tissue to be examined on the spectrum of the x-ray radiation, and thus on the value of the tube voltage of the x-ray tube, is stored in a data memory for different examination types of patients and/ or for different tissues to be examined. An examination type is thereby always linked with a tissue, such that the examination type is essentially synonymous with the tissue to be examined (which can also be understood as a tissue composition). The dependency of the contrast of the different examination types or of the different tissues to be examined on the spectrum of the x-ray radiation or on the value of the tube voltage of the x-ray tube has been determined in advance by simulations or by calibration measurements, for example using appropriate phantoms, and is stored so as to be available for retrieval in the aforementioned data memory or, respectively, a database. The dependency of the contrast of the defined tissue to be examined on the spectrum of the x-ray radiation or on the value of the tube voltage of the x-ray tube is accordingly learned (obtained) from this data memory for the respective current examination case.

According to an embodiment of the invention, the examination type and/or the defined tissue to be examined is manually provided by the user at the x-ray device. Alternatively, the examination type and/or the defined tissue to be examined can be learned from a scan protocol (that includes the examination type and/or the defined tissue to be examined) for examination of the patient, or from an electronic patient record (including the examination type and/or the defined tissue to be examined) of the patient of a hospital or radiology information system. Since the examination type and/or the defined tissue to be examined are thus known, the parameterization of the tissue contrast, and the corresponding dependency of the contrast of the defined tissue to be examined, on the spectrum of the x-ray radiation, or on the value of the tube voltage of the x-ray tube, can be learned from the aforementioned data memory.

According to another embodiment of the invention, the specification of the dependency of the contrast of the defined tissue to be examined on the spectrum of the x-ray radiation, or on the value of the tube voltage of the x-ray tube, is based on the fact that the spectral dependency of a tissue can generally be represented as a linear combination of the known spectral dependencies of two known different chemical elements or materials. The selection of the examination type and/or the defined tissue to be examined takes place by a setting indicator that can be set between the two known different chemical elements or materials. The setting indicator can be a slider and a scale representing examination types and/or tissue. The parameterization of the tissue contrast is thereby mapped to a one-dimensional problem in the form of adjustment of the slider, which can be realized in a graphical user interface, for example.

According to another embodiment of the invention, the first chemical element is water and a second chemical element is iodine. Positions between the end positions of water or iodine represent mixtures of water and iodine with different proportions with which the contrast of the defined tissue can respectively be associated at defined points of the scale.

For the further determination of the tube voltage, the contrast-to-noise ratio determined for the defined tissue to be examined is kept constant, which contrast-to-noise ratio belongs to the reference voltage and the reference current and/or to the reference noise level.

In another embodiment of the invention, the respective associated tube current is furthermore determined for a constantly maintained contrast-to-noise ratio, thus for a uniform image quality for the different tube voltages that can be set or that are in question.

In order to be able to determine the various tube currents belonging to the different potentially suitable tube voltages, in addition to the dependency of the contrast on the value of the tube voltage (which dependency was already provided for the defined tissue to be examined) the dependency of the noise on the value of the tube voltage and the tube current is to be provided for the defined tissue to be examined. The dependency of the noise on the value of the tube voltage and the tube current for the defined tissue to be examined can have been determined in advance by computer simulations or by calibration measurements, for example using compared phantoms, and be kept available for retrieval in a data memory or a data bank. The dependency of the noise on the tube voltage is preferably determined respectively for different tube voltages and stored in the data memory.

Finally, based on this the tube current at which the contrast-to-noise ratio is constant for the defined tissue to be examined can be determined respectively for the different tube voltages that can be set, or respectively for all potential tube voltages in question.

According to a further embodiment of the invention, under consideration of the respective determined tube current at least one value for the dose of x-ray radiation to be applied to the patient is respectively determined for the different tube voltages that can potentially be set. For a computed tomography apparatus as the x-ray device, the CTDI ("Computer Tomography Dose Index") value and/or the DLP ("Dose Length Product") value are determined as a value for the dose of x-ray radiation that is to be applied to the patient.

In computed tomography the CTDI value indicates the dose in milligrays (mGy) that is applied to a patient in an acquisition slice. If the CTDI value is multiplied with the length of the examination volume, the DLP value is obtained, i.e. the dose of x-ray radiation that is applied to a patient in the course of a scan.

Based on the dose value belonging to each tube voltage that can potentially be set, that tube voltage can already be determined at which the dose of x-ray radiation applied to the patient is minimal, given a uniform image quality or while complying with the desired, predetermined image quality. However, additional acquisition parameters (for example the tube current) that belong to each tube voltage must still be checked for whether they can be set at the x-ray device, or for their technical permissibility.

According to a further embodiment of the invention, for each tube voltage that can potentially be set, a conflict value is determined in relation to the additional acquisition parameters of the x-ray device that belong to the respective tube voltage and that are to be set. This conflict value indicates whether the examination of the defined tissue to be examined of the patient can be implemented with the additional acquisition parameters within the system limits of the x-ray device. For each parameter configuration, a conflict value therefore exists that can in principle be freely defined. For example, a scale from zero to ten could be established for the conflict value, wherein the value zero could indicate "no conflict" (thus that implementation is possible without any problems) and the value ten could indicate "highest conflict", or impossible. The parameter configurations can be classified in this manner.

In a further variant of the above embodiment, the tube voltage at which the lowest dose of x-ray radiation is applied to the patient to examine the defined tissue, and that has a conflict value according to which the examination of the defined tissue of the patient can be implemented with the additional acquisition parameters within the known system limits of the x-ray device, without conflict or with the least conflict, is selected from the tube voltages that can potentially be set. If the examination should be implementable with a low conflict value, the acquisition parameter or parameters causing the conflict would be limited to just the values still permissible within the system limits.

The above object also is achieved in accordance with the present invention by a non-transitory, computer-readable data storage medium that, when the data storage medium is loaded into a computerized control unit of an x-ray device, caused the x-ray device to be operated to execute one or more embodiments of the method described above.

DESCRIPTION OF THE PREFERRED EMBODIMENTS

Figure 1:
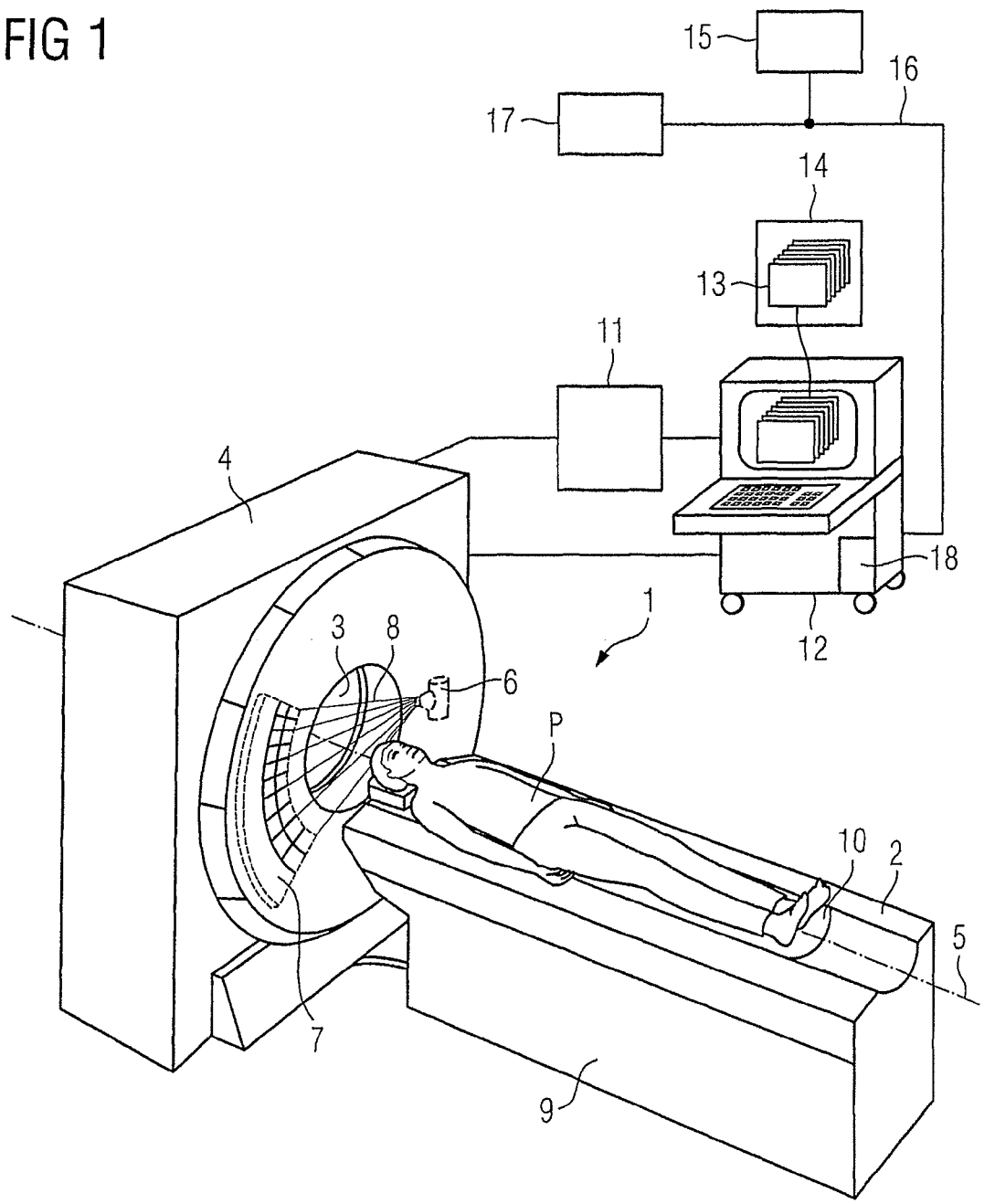
FIG. 1 schematically illustrates a computed tomography apparatus operable in accordance with the invention.

A computed tomography apparatus 1 that is suitable to execute the method according to the invention is shown in FIG. 1. The computed tomography apparatus 1 has a patient bed 2 to support a patient P to be examined. The computed tomography apparatus 1 also has a gantry 4 with a tube/detector system mounted so that it can rotate around a system axis 5. The tube/detector system has an x-ray tube 6 and an x-ray detector unit 7 situated opposite one another. In operation, x-ray radiation 8 emanates from the x-ray tube 6 in the direction of the x-ray detector unit 7 and is detected by the detector unit 7.

The patient bed 2 has a bed base 9 on which a patient support plate 10 is provided on which the patient P lies. The patient support plate 10 is adjustable relative to the bed base 9 so that the patient bearing plate 10 with the patient P thereon can be introduced into the opening 3 of the gantry 4 to acquire x-ray projections of the patient P, for example for a topogram or in a spiral scan. The computational processing of the x-ray projections, for example the generation of a topogram, a slice image or the reconstruction of a volume data set of a body region or of specific tissue of the patient P based on the x-ray projections, takes place in an image computer 11 (schematically shown) of the computed tomography apparatus 1.

The computed tomography apparatus 1 also has a computer 12 with which computer programs for operation and control of the computed tomography apparatus 1 are executed. The computer 12 does not need to be fashioned as a separate computer 12; rather, it can be integrated into the computed tomography apparatus 1.

In the exemplary embodiment of the invention, a scan or an examination of a defined tissue (the liver tissue of the patient P, for example) should be implemented, and without the administration of contrast agent. An examination means the generation of images (slice images of the liver of the patient P in the exemplary embodiment of the invention) the evaluation of which forms the basis of a clinical diagnosis or answering a clinical question. For the generation of the slice images, as low a dose of x-ray radiation as possible should be applied to the patient P while maintaining an image quality that is required or desired for the clinical diagnostic or the solution to the clinical question.

For this purpose, the computer 12 is provided with a computer program 13 with which the value of that tube voltage of the x-ray tube 6 can be determined that, when set and used, causes an optimally low, or the lowest, dose of x-ray radiation to be applied to the patient P during the acquisition of the x-ray projections of the body region of the patient P that includes the liver. The computer program 13 thereby causes the method described in the following to determine the aforementioned tube voltage to be executed. The control commands (programming instructions) for implementing the method can be loaded into the computer 12 from a portable storage medium (for example from a CD 14 or a memory stick) or from a server 15 (as a data medium) via a network 16.

Through a graphical user interface (not shown) of the computer 12, a user can enter the examination type, thus a liver examination or the liver as the defined tissue to be examined. Alternatively, the user can directly select a scan protocol for the examination of a liver. The selection of a scan protocol for examination of a liver can also take place based on the electronic patient record of the patient P that, for example, can be retrieved via the network 16 from an HIS 17 (Hospital Information System) or RIS 17 (Radiology Information System) and from which the examination of the liver that is to be implemented is learned.

Figure 2:
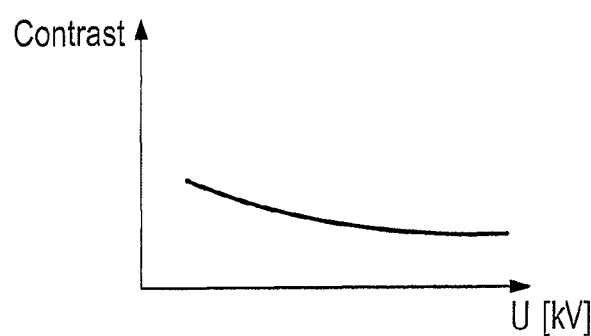
FIGS. 2 through 5 are diagrams for explaining the method according to the invention.

Since the examination of the liver or the examination of liver tissue is known in one of these ways, the data about the dependency of the image contrast of liver tissue on the spectrum of the x-ray radiation or on the tube voltage can be learned from a data memory 18 of the computer 12. Since the tube voltage is determinative for the spectrum of x-ray radiation, only the tube voltage is discussed in the following. The dependency of the image contrast of liver tissue on the tube voltage U (as can be learned from the data memory 18) is schematically illustrated in the diagram of FIG. 2. However, the data do not necessarily need to be provided as a diagram; rather, they can also be stored for retrieval in the data memory 18 as a table or in another suitable form.

Furthermore, the dependency of the image noise on the tube voltage U and on the tube current is stored for retrieval in the data memory 18. In the exemplary embodiment of the invention, the dependency of the noise on the tube voltage has been determined in the form of a curve progression for liver tissue, meaning that a tube current belonging to a defined noise level and a defined tube voltage can be determined from the curve progression. The data can also be stored for retrieval in the data memory 18 in table form or in another suitable manner.

The correlations between image contrast and tube voltage as well as between image noise, tube voltage and tube current that are stored in the data memory 18 have been determined in advance for different phases of different tissue by computer simulations or calibration measurements, for example using phantoms prepared to correspond to the respective tissue.

Alternatively, the parameterization of the image contrast of the liver tissue can be produced with a slider of the graphical user interface, with which slider a scale is associated that represents examination types and/or tissues. Use is made of the fact that the spectral dependency of a tissue or material can generally be represented as a linear combination of the known spectral dependencies on two known, different chemical elements or materials. This is possible because the absorption of x-ray radiation is essentially always determined by the photoelectric effect and the Compton effect. Water (which forms the first end of the scale) and iodine (which forms the second end of the scale) suggest themselves as characteristic materials or chemical elements. Positions between the end positions of water or iodine represent mixtures of water and iodine with different proportions with which the contrast of a defined tissue or a defined tissue composition can be associated at defined points according to the scale.

In a further preparation of the scan of the liver of the patient P, in the exemplary embodiment of the invention a topogram of the body region of the patient P that includes the liver is acquired with the computed tomography apparatus 1 in a known manner.

The scan protocol for the examination of the liver normally already includes a suggestion for the tube voltage and the tube current that are to be set for the scan of liver tissue. Using the topogram, the user can accept these or adapt them as necessary with regard to the desired image quality for the slice images of the liver tissue that are to be generated. In this way a reference protocol with a reference tube voltage and a reference tube current is provided by the user. Alternatively or additionally, a reference value for the level of allowable image noise for the slice images to be generated can be provided by the user as an image quality parameter.

Figure 3:
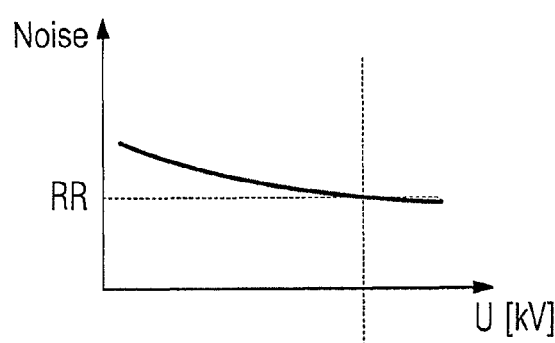
Figure 4:
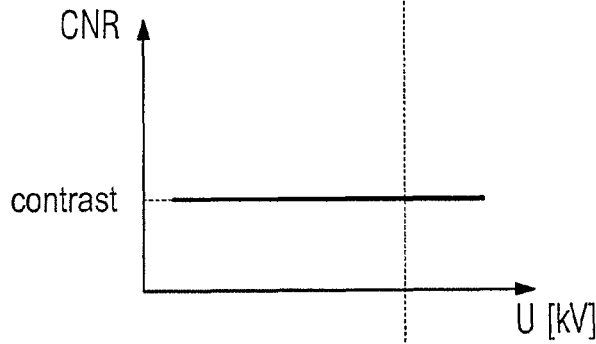

To further determine the tube voltage, the contrast-to-noise ratio for the liver tissue is held constant under consideration of the reference tube voltage and the reference tube current and/or the reference value of the image noise. The reference tube voltage and the reference tube current and/or the reference value of the image noise thus establish the contrast-to-noise ratio that is to be held constant as an image quality feature for non-varying image quality given varying tube voltage. In FIG. 3 the reference tube voltage RF and the reference noise level RR are plotted as examples. The constantly maintained contrast-to-noise ratio CNR for the liver tissues, based on the reference tube voltage RF and the reference noise level RR, is illustrated in FIG. 4. FIG. 3 shows the dependency of the noise on the tube voltage for the constantly maintained contrast-to-noise ratio CNR, which dependency was determined for the constantly maintained contrast-to-noise ratio CNR from the aforementioned dependency of the noise on the tube voltage and the dependency of the contrast on the tube voltage for liver tissue that were determined for different tube currents.

For each of the potential tube voltages of the x-ray tube 6 that are considered for the examination of the liver tissue, the associated tube current is determined given a constantly maintained contrast-to-noise ratio for the liver tissue. Depending on how the image contrast and the image noise for the liver tissue change given different tube voltages, a different tube current results so that the contrast-to-noise ratio is constant as was predetermined.

Figure 5:
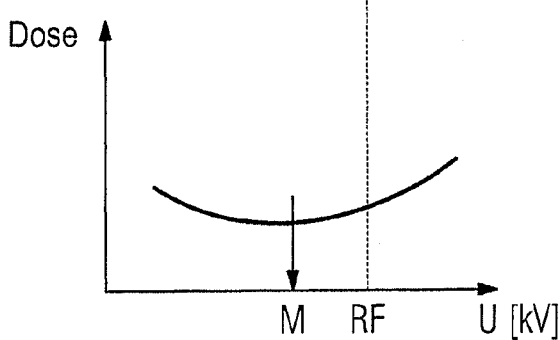

If the tube currents belonging to the different potential tube voltages in question are determined, for each potential tube voltage that can be set at least one value for the dose of x-ray radiation to be applied to the patient is respectively determined under consideration of the respectively determined tube current. In the case of the present exemplary embodiment of the invention, for each potential tube voltage in question the CTDI value or, respectively, the computed tomography dose index is determined as a dose value and the DLP value or, respectively, dose length product is determined, wherein the latter results from the CTDI value via multiplication with the length of the examination volume. In FIG. 5 the DLP values belonging to the potential tube voltages U in question are plotted over the tube.

In principle, by determining the minimum M of the curve of the diagram of FIG. 5 that tube voltage can be identified given whose use for the scan of the body region of the patient comprising the liver the lowest dose of x-ray radiation is applied to the patient while maintaining the desired image quality.

However, since additional acquisition parameters (such as the tube current etc.) belong to each tube voltage, it must additionally be checked with which potentially suitable tube voltage—together with associated additional acquisition parameters—the scan with the computed tomography apparatus 1 can even be implemented within the system limits of the computed tomography apparatus 1.

In the exemplary embodiment of the invention, a conflict value (that indicates whether the examination of the liver tissue of the patient P with the additional acquisition parameters can be implemented within the system limits of the computed tomography apparatus 1) is determined for each potential tube voltage in question and its associated additional acquisition parameters. For example, it must be checked whether the tube current belonging to a potential tube voltage in question exceeds the maximum allowable tube current at the system, or whether the maximum allowable tube load for the duration of the scan is exceeded. If an overrun occurs for a parameter configuration, in the exemplary embodiment of the invention, a conflict value between zero and ten is assigned depending on the scale of the overrun, wherein the value zero means "no conflict", thus that implementation can occur without any problems, and the value ten means "highest conflict" or, respectively, unfeasible.

If a conflict value exists for each parameter configuration, a tube voltage is selected, from among the tube voltages in question that can potentially be set, at which the lowest dose of x-ray radiation is applied to the patient P for examination of the liver tissue, and that has a conflict value according to which the examination of the liver tissue of the patient can be implemented within the system limits of the computed tomography apparatus with the additional acquisition parameters belonging to the tube voltage without conflict or with the least conflict. If the examination can be implementable with only a small conflict value, the acquisition parameters causing the conflict are limited to just allowable values within the system limits.

The invention was described in the preceding in an example of liver tissue, but the method according to the invention is not limited to liver tissue and can be implemented for any other tissue.

Although modifications and changes may be suggested by those skilled in the art, it is the intention of the inventor to embody within the patent warranted hereon all changes and modifications as reasonably and properly come within the scope of his contribution to the art.

We claim as our invention:

1. A method for operating an x-ray device comprising an x-ray tube operable with a tube voltage, comprising:
   providing a computerized control unit of said x-ray device with at least one parameter that establishes or describes a desired image quality of defined tissue of a patient to be examined with said x-ray device;
   in said control unit, determining a value of the tube voltage of the x-ray tube to generate at least one image of said defined tissue with said image quality, based on a dependency of a contrast of the defined tissue on a spectrum of x-ray radiation emitted by said x-ray tube associated with said value of said tube voltage, and to maintain a contrast-to-noise ratio that achieves the image quality designated or described by said parameter while simultaneously producing a dose of x-ray radiation applied to the patient that is as low as possible; and
   from said control unit, setting a value of said tube voltage, as a set value of said tube voltage, at said x-ray tube and operating said x-ray tube and said x-ray device to acquire at least one x-ray projection of said defined tissue, with said set value of said tube voltage, to generate at least one image of said defined tissue with said image quality.

2. A method as claimed in claim 1 comprising, from said computerized control unit, operating said x-ray device with a reference protocol to acquire at least one x-ray projection of said defined tissue, said reference protocol comprising operation of said x-ray tube with a reference tube voltage and an associated reference tube current as said parameter establishing or describing said image quality.

3. A method as claimed in claim 1 comprising employing, as said parameter that establishes or describes said image quality, a reference noise in an image of said defined tissue.

4. A method as claimed in claim 1 comprising storing, in a data memory, a dependency of a contrast of said defined tissue on a spectrum of x-ray radiation emitted by said x-ray tube at said value of said tube voltage, for each of different defined tissues and accessing said dependency from said data memory by said computerized control unit.

5. A method as claimed in claim 1 comprising manually entering a designation into said computerized control unit of said defined tissue to be examined.

6. A method as claimed in claim 1 comprising, from said computerized control unit, accessing an electronic patient record of a hospital or radiology information system that includes a designation of the defined tissue to be examined, and using the defined tissue in said electronic patient record as said defined tissue to be examined in said computerized control unit.

7. A method as claimed in claim 1 comprising operating said x-ray device to implement a scan protocol and analyzing said scan protocol to identify said defined tissue to be examined.

8. A method as claimed in claim 1 comprising operating a setting element of said computerized control unit to specify the dependency of the contrast of the defined tissue on the spectrum of the x-ray radiation produced by the value of the tube voltage, as a linear combination of known spectral dependencies of two known, different chemical elements or materials.

9. A method as claimed in claim 8 comprising employing a slider as said setting element, comprising a scale representing, at opposite scale ends, different examination types, different tissues, and different phases of tissues.

10. A method as claimed in claim 8 wherein a first of said two known, different chemical elements or materials as water, and a second of said two known, different chemical elements or materials is iodine.

11. A method as claimed in claim 1 comprising also setting a tube current that is respectively determined for different tube voltages that can be set.

12. A method as claimed in claim 11 comprising, in said computerized control unit, determining at least one value for a dose of said x-ray radiation applied to the patient from said different tube voltages that can be set and the respective tube currents determined therefor.

13. A method as claimed in claim 12 comprising determining a value for said dose as at least one of a computed tomography dose index (CTDI) value, and a dose length product (DLP).

14. A method as claimed in claim 11 comprising, in said computerized control unit, for each tube voltage that can be set, determining a conflict value in relation to additional acquisition parameters of the x-ray device associated with the respected tube voltage, said conflict value indicating whether acquisition of said at least one x-ray projection of said defined tissue can be implemented with said additional acquisition parameters within system limits of said x-ray device.

15. A method as claimed in claim 14 comprising, in said computerized control unit, selecting a tube voltage, from among said tube voltages that can be set, for which a lowest dose of x-ray radiation is applied to the patient to acquire said at least one x-ray projection of said defined tissue, and that has a conflict value indicating that the acquisition of said at least one x-ray projection of the defined tissue can be implemented with the additional acquisition parameters within said system limits of said x-ray device, without conflict or with a least conflict.

16. An x-ray imaging system comprising:
x-ray device comprising an x-ray tube operable with a tube voltage;
a computerized control unit of said x-ray device that is provided with at least one parameter that establishes or describes a desired image quality of defined tissue of a patient to be examined with said x-ray device;
said control unit being configured to determine a value of the tube voltage of the x-ray tube to generate at least one image of said defined tissue with said image quality, based on a dependency of a contrast of the defined tissue on a spectrum of x-ray radiation emitted by said x-ray tube associated with said value of said tissue voltage, and to maintain a contrast-to-noise ratio that achieves the image quality designated or described by said parameter while simultaneously producing a dose of x-ray radiation applied to the patient that is as low as possible; and
said control unit being configured to set a value of said tube voltage, as a set value of said tube voltage, at said x-ray tube and to operate said x-ray tube and said x-ray device to acquire at least one x-ray projection of said defined tissue, with said set value of said tube voltage, to generate at least one image of said defined tissue with said image quality.

17. A non-transitory, computer-readable data storage medium encoded with programming instructions, said data storage medium being loaded into a computerized control device of an x-ray device, that includes an x-ray tube operable with a tube current, said programming instructions causing said computerized control unit to:
receive as an input at least one parameter that establishes or describes a desired image quality of defined tissue of a patient to be examined with said x-ray device;
determine a value of the tube voltage of the x-ray tube to generate at least one image of said defined tissue with said image quality, based on a dependency of a contrast of the defined tissue on a spectrum of x-ray radiation emitted by said x-ray tube associated with said value of said tissue voltage, and to maintain a contrast-to-noise ratio that achieves the image quality designated or described by said parameter while simultaneously producing a dose of x-ray radiation applied to the patient that is as low as possible; and
set a value of said tube voltage, as a set value of said tube voltage, at said x-ray tube and operate said x-ray tube and said x-ray device to acquire at least one x-ray projection of said defined tissue, with said set value of said tube voltage, to generate at least one image of said defined tissue with said image quality.

* * * * *